United States Patent
Ciszewski et al.

(10) Patent No.: US 6,897,307 B2
(45) Date of Patent: May 24, 2005

(54) PROCESS FOR PREPARING 2,6-DIAMINOPURINE DERIVATIVES

(75) Inventors: Lech Andrzej Ciszewski, Morristown, NJ (US); Liladhar M. Waykole, Succasunna, NJ (US)

(73) Assignee: Novartis AG, Basel (CH)

(*) Notice: Subject to any disclaimer, the term of this patent is extended or adjusted under 35 U.S.C. 154(b) by 60 days.

(21) Appl. No.: 10/401,349

(22) Filed: Mar. 28, 2003

(65) Prior Publication Data

US 2003/0225278 A1 Dec. 4, 2003

Related U.S. Application Data

(60) Provisional application No. 60/368,304, filed on Mar. 28, 2002.

(51) Int. Cl.$^7$ .................... C07D 473/16; C07D 473/40
(52) U.S. Cl. ........................................ 544/277
(58) Field of Search ........................................ 544/277

(56) References Cited

U.S. PATENT DOCUMENTS 4,954,504 A * 9/1990 Chen et al. .................. 544/277

FOREIGN PATENT DOCUMENTS

WO          01/09134          2/2001

OTHER PUBLICATIONS

Kelley et al., "Synthesis and Structure–Activity Relationships of 2–Substituted–6–(dimethylamino)–9–(4–methylbenzyl)–9H–purines with Antirhinovirus Activity", J. Med. Chem., vol. 32, pp. 218–224 (1989).

Nugiel et al., "Facile Preparation of 2,6–Disubstituted Purines Using Solid–Phase Chemistry", J. Org. Chem., vol. 62, pp. 201–203 (1997).

Brill et al., "Solid–Phase Synthesis of 2,6,8–Trisubstituted Purines", Tetrahedron Letters, vol. 42, pp. 6515–6518 (2001).

* cited by examiner

*Primary Examiner*—Mark L. Berch
(74) *Attorney, Agent, or Firm*—Thomas R. Savitsky; John D. Thallemer; Paivi J. Kukkola

(57) ABSTRACT

A one-pot process for preparing 2,6-diaminopurine derivatives or an acid addition salt thereof comprising: (i) reacting a purine compound with an amine compound in the presence of a tertiary amine at a pH of 7 to 14 to form a 6-substituted aminopurine derivative, and (ii) reacting the 6-substituted aminopurine with an aromatic amine in the presence of an acid catalyst at a pH of 0.1 to less than 7.

30 Claims, No Drawings

PROCESS FOR PREPARING 2,6-DIAMINOPURINE DERIVATIVES

This application claims the benefit of U.S. Provisional Application Ser. No. 60/368,304, filed Mar. 28, 2002.

Purine derivatives have received great attention due to their potential as target nucleotide-binding proteins, which play a significant role in many biological processes. Many of the purine libraries focus on variations at the 2- and 6-position. WO 01/09134 A1 describes the preparation and use of purine derivatives such as 2,6-diaminopurine which has been shown to inhibit the protein tyrosine kinase syk which is critical for signaling through the IgE receptor, leading to mast cell degranulation and activation, which is important in treating asthma and allergic rhinitis. The purine derivatives described in the examples of WO 01/09134 A1 are prepared under basic conditions and at a temperature ranging from 90° C. to 190° C.

Nugiel et al., "Facile Preparation of 2,6-Disubstituted Purines Using Solid-Phase Chemistry", *J. Organic Chem.*, Vol. 62, pp. 201–203 (1997) states on page 201, column 2, that "[t]he 6-chloro position was the more reactive site and was easily displaced with 5 equivalents of benzylamine and 5 equivalents of triethylamine at 80° C. in 1-butanol after 3 hours" . . . "The 2-chloro substituent was much less reactive and required more severe reaction conditions." This was accomplished using the amine as a solvent and heating the resin at 150° C. for 2.5 hours.

Wolfgang et al., "Solid-Phase Synthesis of 2,6,8-Trisubstituted Purines", *Tetrahedron. Lett.*, Vol. 42, pp. 6515–6518 (2001) displaces the chlorine atom at the 2-position with an amine at 125° C.

Kelley et al., "Synthesis and Structure-Activity Relationships of 2-Substituted-6-(Dimethylamino)-9-(4-Methylbenzyl)-9H-Purines With Antirhinovirus Activity", *J. Med. Chem.*, Vol. 32, pp. 218–224 (1989) displaces the chlorine atoms at the 2-position with amines at 116° C. under reduced pressure for 65 hours.

The invention provides a process for preparing 2,6-diaminopurine derivatives or acid addition salts thereof comprising:

(i) reacting a purine compound having formula (V)

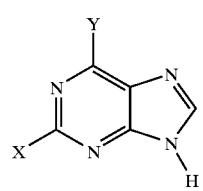

(V)

with an amine compound having formula (VI)

(VI)

in the presence of a tertiary amine at a pH of 7 to 14 and preferably at a temperature of about 20° C. to about 150° C., more preferably 50° C. to about 130° C., most preferably 70° C. to about 90° C., to form a 6-substituted aminopurine derivative having formula (I)

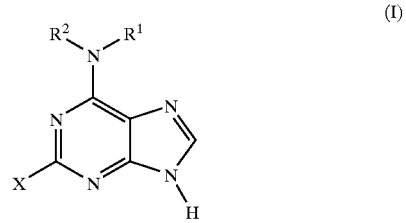

(I)

wherein X and Y are, independently, a halogen, preferably chlorine; and (ii) reacting the 6-substituted aminopurine derivative with an aromatic amine having formula (II)

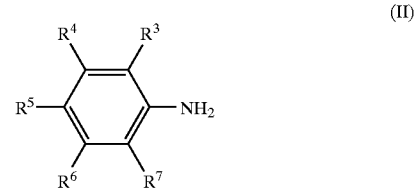

(II)

in the presence of an acid catalyst at a pH of 0.1 to less than 7, preferably at a temperature of about 20° C. to about 180° C., more preferably 50° C. to about 140° C., most preferably 70° C. to about 90° C., to form a 2,6-diaminopurine derivative having formula (III) or acid addition salt thereof

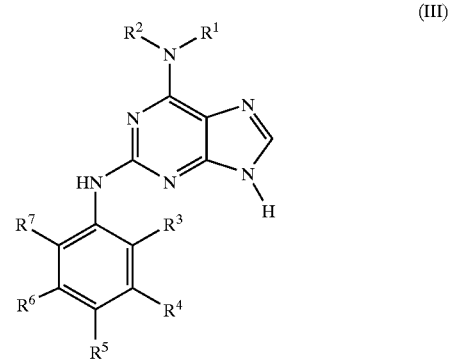

(III)

wherein
X is a halogen;
$R^1$ and $R^2$ are, independently, selected from the group consisting of hydrogen, alkyl, alkenyl, cycloalkyl, benzocycloalkyl, cycloalkylalkyl, aralkyl, heterocyclic group, alkoxy, and a group having formula (IV)

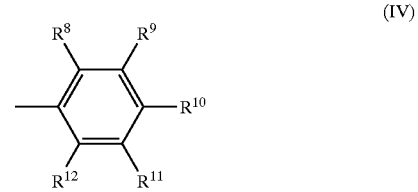

(IV)

$R^3$, $R^4$, $R^5$, $R^6$, $R^7$ $R^8$, $R^9$, $R^{10}$, $R^{11}$ and $R^{12}$ are, independently, selected from the group consisting of hydrogen, halogen, alkyl, alkoxy, —N($R^{13}$)$R^{14}$, —SO$_2$N($R^{15}$)$R^{16}$, C$_1$–C$_4$alkylene-SO$_2$N($R^{15}$)$R^{16}$ and —CON($R^{17}$)$R^{18}$; or, when $R^1$ and $R^2$, or two of $R^3$, $R^4$, $R^5$, $R^6$, $R^7$ $R^8$, $R^9$, $R^{10}$, $R^{11}$ and $R^{12}$, are attached to adjacent carbon atoms on the indicated benzene rings, they denote, together with the carbon atoms to which they are attached, a carbocyclic group having 5- to 10-ring atoms or a heterocyclic group having 5- to 10-ring atoms of which one, two or three are hetero atoms selected from the group consisting of nitrogen, oxygen and sulfur; $R^{13}$ is alkyl; $R^{14}$ is alkyl or —$COR^{19}$ wherein $R^{19}$ is selected from the group consisting of alkyl, haloalkyl, alkoxy, alkoxyalkyl, alkoxycarbonyl, and alkoxycarbonylalkyl; or $R^{13}$ and $R^{14}$, together with the nitrogen atom to which they are attached, denote a heterocyclic group having 5- or 6-ring atoms of which one or two are hetero atoms selected from nitrogen, oxygen and sulfur; $R^{15}$ is hydrogen or alkyl; $R^{16}$ is selected from the group consisting of hydrogen, alkyl, hydroxyalkyl, alkoxyalkyl, and alkoxycarbonylalkyl; or $R^{15}$ and $R^{16}$ together with the nitrogen atom to which they are attached denote a heterocyclic group having 5- or 6-ring atoms of which one or two are hetero atoms selected from nitrogen, oxygen and sulfur; and $R^{17}$ and $R^{18}$ are independently hydrogen or alkyl.

As used herein, "alkyl" means straight chain or branched alkyl, which may be, for example, $C_1$–$C_{10}$-alkyl such as methyl, ethyl, n-propyl, isopropyl, n-butyl, isobutyl, sec-butyl, tert-butyl, straight or branched pentyl, straight or branched hexyl, straight or branched heptyl, straight or branched nonyl or straight or branched decyl. Preferably alkyl is $C_1$–$C_4$-alkyl.

"Alkoxy" means straight chain or branched alkoxy and may be, for example, $C_1$–$C_{10}$alkoxy such as methoxy, ethoxy, n-propoxy, isopropoxy, n-butoxy, isobutoxy, sec-butoxy, tert-butoxy, or straight or branched pentoxy, hexyloxy, heptyloxy, octyloxy, nonyloxy or decyloxy. Preferably alkoxy is $C_1$–$C_4$alkoxy.

"Alkenyl" means straight chain or branched alkenyl, which may be, for example, $C_2$–$C_{10}$alkenyl such as vinyl, 1-propenyl, 2-propenyl, 1-butenyl, isobutenyl, or straight or branched pentenyl, hexenyl, heptenyl, octenyl, nonenyl or decenyl. Preferred alkenyl is $C_2$–$C_4$alkenyl.

"Cycloalkyl" means $C_3$–$C_{10}$-cycloalkyl having 3- to 8-ring carbon atoms and may be, for example, cyclopropyl, cyclobutyl, cyclopentyl, cyclohexyl, cycloheptyl or cycloheptyl, any of which can be substituted by one, two or more $C_1$–$C_4$-alkyl groups, particularly methyl groups. Preferably, cycloalkyl is $C_3$–$C_6$-cycloalkyl.

"Benzocycloalkyl" means cycloalkyl (e.g., one of the $C_3$–$C_{10}$-cycloalkyl groups mentioned hereinbefore), attached at two adjacent carbon atoms to a benzene ring. Preferably, benzocycloalkyl is benzo-$C_5$–$C_6$-cycloalkyl, especially benzocyclohexyl (tetrahydronaphthyl).

"Cycloalkylalkyl" means $C_3$–$C_{10}$-cycloalkyl-$C_1$–$C_{10}$-alkyl where the $C_3$–$C_{10}$-cycloalkyl group has 3- to 8-ring carbon atoms and may be, for example, one of the $C_1$–$C_{10}$-alkyl groups mentioned hereinbefore, particularly one of the $C_1$–$C_4$-alkyl groups, substituted by one of the $C_3$–$C_{10}$-cycloalkyl groups mentioned hereinbefore. Preferably cycloalkylalkyl is $C_3$–$C_6$-cycloalkyl-$C_1$–$C_4$-alkyl.

"Aralkyl" means $C_6$–$C_{10}$-aryl-$C_1$–$C_{10}$-alkyl and may be, for example, one of the $C_1$–$C_{10}$-alkyl groups mentioned hereinbefore, particularly one of the $C_1$–$C_4$-alkyl groups, substituted by phenyl, tolyl, xylyl or naphthyl. Preferably, aralkyl is phenyl-$C_1$–$C_4$-alkyl, particularly benzyl or 2-phenylethyl.

"Heterocyclyl" means a monovalent heterocyclic group having up to 20 carbon atoms and one, two, three or four heteroatoms selected from nitrogen, oxygen and sulfur, the group optionally having an alkyl, alkylcarbonyl, hydroxyalkyl, alkoxyalkyl or aralkyl group attached to a ring carbon or nitrogen atom and being linked to the remainder of the molecule through a ring carbon atom, and may be, for example, a group, preferably a monocyclic group, with one nitrogen, oxygen or sulfur atom such as pyrryl, pyridyl, piperidyl, furyl, tetrahydrofuryl or thienyl, or a group, preferably a monocyclic group, with two hetero atoms selected from nitrogen, oxygen and sulfur, such as imidazolyl, pyrimidinyl, piperazinyl, oxazolyl, isoxazolyl, thiazolyl, morpholinyl or thiomorpholinyl. Preferably, heterocyclyl is a monocyclic group having 5- or 6-ring atoms and one or two nitrogen atoms, or one nitrogen atom and one oxygen atom, in the ring and optionally substituted on a ring nitrogen atom by $C_1$–$C_4$-alkyl, hydroxy-$C_1$–$C_4$-alkyl, $C_1$–$C_4$-alkylcarbonyl or phenyl-$C_1$–$C_4$-alkyl.

"Alkoxyalkyl" means straight chain or branched alkyl substituted by one or more alkoxy groups and may be, for example, a $C_1$–$C_{10}$-alkoxy-$C_1$–$C_{10}$-alkyl group, such as one of the $C_1$–$C_{10}$-alkyl groups, particularly one of the $C_1$–$C_4$-alkyl groups, mentioned hereinbefore substituted by one of the $C_1$–$C_{10}$-alkoxy groups, preferably one of the $C_1$–$C_4$-alkoxy groups, mentioned hereinbefore. Preferably alkoxyalkyl is $C_1$–$C_4$-alkoxy-$C_1$–$C_4$-alkyl.

"Alkylcarbonyl" means a group $R^{20}CO$ wherein $R^{20}$ is alkyl, for example, $C_1$–$C_{10}$-alkyl such as one of the $C_1$–$C_{10}$-, preferably $C_1$–$C_4$-, alkyl groups mentioned hereinbefore. Preferably, alkylcarbonyl is $C_1$–$C_4$-alkylcarbonyl, i.e., $R^{20}CO$ where $R^{20}$ is $C_1$–$C_4$-alkyl.

"Alkoxycarbonyl" means a group $R^{21}CO$ wherein $R^{21}$ is an alkoxy group, for example, a $C_1$–$C_{10}$-alkoxy group such as one of the $C_1$–$C_{10}$-, preferably $C_1$-$C_4$, alkoxy groups mentioned hereinbefore. Preferably, alkoxycarbonyl is $C_1$–$C_4$-alkoxycarbonyl, i.e., $R^{21}CO$ where $R^{21}$ is $C_1$–$C_4$-alkoxy.

"Alkoxycarbonylalkyl" means straight or branched chain alkyl, for example, a $C_1$–$C_{10}$-alkyl group such as one of the $C_1$–$C_{10}$-, preferably $C_1$–$C_4$-, alkyl groups mentioned hereinbefore, substituted by an alkoxycarbonyl group as hereinbefore defined. Preferably, alkoxycarbonylalkyl is $C_1$–$C_4$-alkoxy-carbonyl-$C_1$–$C_4$-alkyl.

"Haloalkyl" means straight chain or branched alkyl, for example, $C_1$–$C_{10}$-alkyl such as one of the $C_1$–$C_{10}$-alkyl groups mentioned hereinbefore, substituted by one or more, for example one, two or three, halogen atoms, preferably fluorine or chlorine atoms. Preferably haloalkyl is $C_1$–$C_4$-alkyl substituted by one, two or three fluorine or chlorine atoms.

"Hydroxyalkyl" means straight chain or branched alkyl, for example, $C_1$–$C_{10}$-alkyl such as one of the $C_1$–$C_{10}$-alkyl groups mentioned hereinbefore, substituted by one, two or three hydroxyl groups. Preferably, hydroxyalkyl is $C_1$–$C_4$-alkyl substituted by one hydroxyl group.

A preferred purine compound is

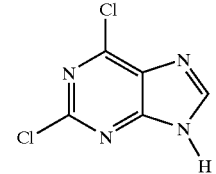

A preferred 6-substituted aminopurine derivative is

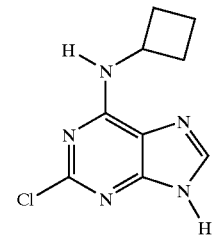

A preferred 2,6-diaminopurine derivative is

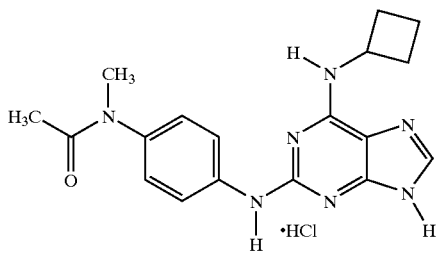

Optionally, a solvent may be used in Step (i) and/or Step (ii). Preferred solvents include $C_3$–$C_{12}$ alcohols such as butanol and pentanol; dimethylformamide, dioxan, tetrahydrofuran, N-methylpyrrolidinone, 2-methoxyethyl ether, and ionic liquids. The solvent used in Step (i) and (ii) may be the same or different. A combination of solvents may also be used. A preferred solvent is n-pentanol or n-butanol.

In one embodiment of the invention, the amine compound having formula (VI) in Step (i) is used as a reagent and a solvent.

The amine compound having formula (VI) is preferable selected from cumidine, anisidine, chloroaniline, bromoaniline, fluoroaniline, cyclobutylamine, cyclohexylamine, cyclopentylamine, and N-(4-aminophenyl)-N-methyl-acetamide. The preferred amine compound having formula (VI) is cyclobutylamine.

Preferably, the tertiary amine used in Step (i) is selected from N,N-diisopropylethylamine, triethylamine, tripropyl amine, tributyl amine, and ethyldimethylamine. A combination of tertiary amines may also be used. Most preferably, the tertiary amine is N,N-diisopropylethylamine.

In one embodiment of the invention, the acid catalyst in Step (ii) is used as a reagent and a solvent.

The acid catalyst is essentially any acid or compound such as triarylsilyl halide, trialkylsilyl halide, and alkylarylsilyl halide, for example, trimethylsilyl chloride and thionyl chloride, which generate an acid in situ by reacting with an alcohol. Suitable acids are a mineral acid, organic carboxylic acid, and organic sulfonic acid. Specific examples of acids are hydrochloric acid, hydrobromic acid, benzoic acid, acetic acid, citric acid, propionic acid, phosphoric acid, fumaric acid, succinic acid, methanesulfonic acid, maleic acid, and sulfuric acid. More preferably, the acid catalyst is hydrochloric acid or trimethylsilyl chloride. A combination of acid catalysts may also be used.

The acid catalyst is present in an amount of from about 0.001 to about 5 moles, based on the moles of the purine compound having formula (V) which is initially present. Preferably, the acid catalyst is present in an amount of from about 0.01 to 2 moles, based on the moles of the purine compound initially present. More preferably, in a step-wise reaction characterized with an isolation step, the acid catalyst is present in an amount of from about 0.01 to about 0.1 moles, and in a one-pot reaction characterized by the presence of base, the acid catalyst is present in an amount of from about 0.5 to about 1.3 moles, based on the moles of the purine compound.

The aromatic amine having formula (II) is preferable selected from cumidine, anisidine, chloroaniline, bromoaniline, fluoroaniline, and N-(4-aminophenyl)-N-methyl-acetamide. The preferred aromatic amine is N-(4-aminophenyl)-N-methyl-acetamide.

It is within the scope of the invention to use a one-pot synthesis or step-wise process for preparing the 2,6-diaminopurine derivatives of the invention.

The 2,6-diaminopurine derivatives are capable of forming acid addition salts, particularly pharmaceutically acceptable acid addition salts. Pharmaceutically acceptable acid addition salts of the 2,6-diaminopurine derivatives include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example, aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid, fumaric acid, or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from 2,6-diaminopurine derivatives by known salt-forming procedures.

The 2,6-diaminopurine derivatives which contain acidic, e.g., carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from 2,6-diaminopurine derivatives by known salt-forming procedures.

The 2,6-diaminopurine derivatives in free or salt form prepared by the process of the invention are useful to inhibit the activity of the tyrosine protein kinase syk, which is an activator of pro-inflammatory cells driving an allergic response. In addition, the 2,6-diaminopurine derivatives are useful in the treatment of inflammatory or obstructive airways diseases.

The following non-limiting examples illustrate further aspects of the invention.

EXAMPLE 1

Preparation of 2-Chloro-N-Cyclobutyl-9H-Purin-6-Amine by a Base Catalyzed Process

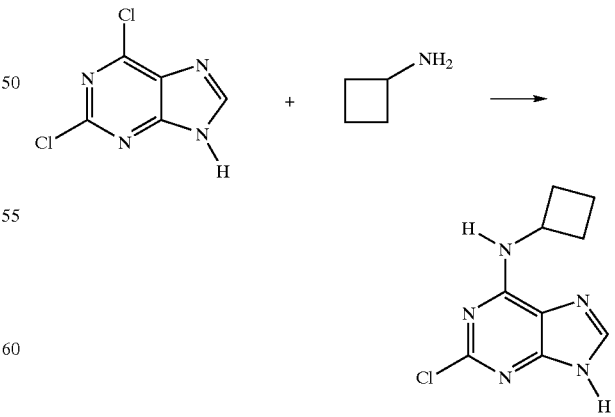

A 12 L, 4-neck, round-bottomed flask fitted with a mechanical stirrer, digital thermometer, heating and cooling capabilities, condenser, addition funnel, and nitrogen inlet and outlet, was flushed with nitrogen and charged with 492.9 g (2.61 moles) of 2,6-dichloro-9H-purine, 497.7 mL (2.87 moles) of N,N-diisopropylethylamine, and 3.65 L of anhydrous 1-butanol. The mixture was stirred and heated to 75° C. and 244.9 mL (2.87 moles) of cyclobutylamine in 1.25 L of anhydrous 1-butanol, was added during about 1 hour at a temperature of 75° C.–77° C. The reaction temperature and stirring was maintained for 4.5 hours. The mixture was cooled to 5° C. over a period of 1 hour. The product was filtered and the filter cake was washed three times with a total of 0.9 L of 1-butanol. The filter cake was collected and dried at 75° C./20 mm Hg for 24 hours to give 506.6 g of light yellow crystalline solid. Theoretical yield was 583.3 g. Actual yield was 86.9%.

EXAMPLE 2

Preparation of N-[4-[[6-(Cyclobutylamino)-9H-purin-2-yl]amino]phenyl]-N-methylacetamide hydrochloride by an Acid Catalyzed Process

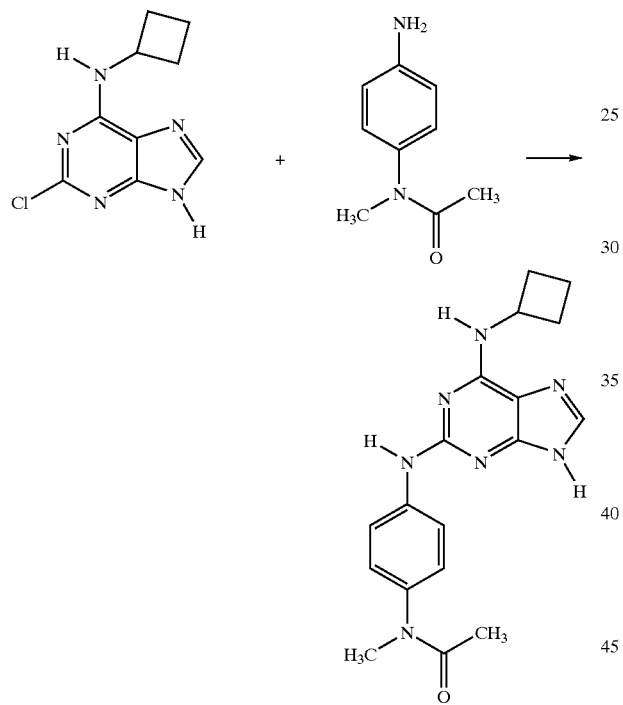

A 5 L, 4-neck, round-bottomed flask fitted with a mechanical stirrer, digital thermometer, heating and cooling capabilities, condenser, addition funnel, and nitrogen inlet and outlet, was flushed with nitrogen and charged with 479.8 g (2.15 moles) of 2-chloro-N-cyclobutyl-9H-purin-6-amine, 387.5 g (2.36 moles) of N-(4-aminophenyl)-N-methylacetamide, and 3.6 L of dry 1-butanol. The mixture was stirred and 2.72 mL (0.02 moles) of chlorotrimethylsilane was added at 25° C. The mixture was heated to 117° C. over about 50 minutes. The reaction temperature and stirring was maintained for 12.5 hours. The mixture was cooled to 50° C. over a period of 2 hours. A temperature of 50° C. was maintained for an additional hour. The product was filtered and the filter cake was washed three times with a total of 1.2 L of 1-butanol. The filter cake was collected and dried at 50° C./20 mm Hg for 24 hours to give 514.3 g of light yellow crystalline solid. Theoretical yield was 832.0 g. Actual yield was 61.8%.

EXAMPLE 3

Preparation of 2,6-Diaminopurine by a One-Pot Synthesis

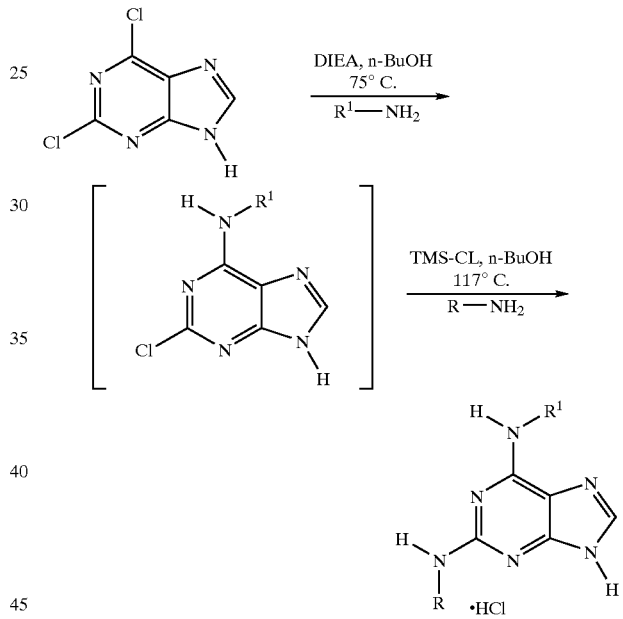

The procedures according to Examples 1 and 2 were used to prepare 2,6-diaminopurine derivatives with different amine compounds, and reaction conditions, as set forth in Table I.

TABLE I

| Exp. | $R^1$ | Time (h) | R | TMS-Cl (eq) | Time (h) | Results/ HPLC/yield |
|---|---|---|---|---|---|---|
| A | —$(CH_2)_3CH_3$ | 2 | | 1.3 | 9 | Reaction complete 67% |

TABLE I-continued

| Exp. | R¹ | Time (h) | R | TMS-Cl (eq) | Time (h) | Results/ HPLC/yield |
|---|---|---|---|---|---|---|
| B Comparative | —(CH$_2$)$_3$CH$_3$ | 2 | 4-MeO-C$_6$H$_4$-CH< | — | 10 | No reaction |
| C | cyclohexyl-CH< | 7 | 4-MeO-C$_6$H$_4$-CH< | 1.3 | 10 | Reaction complete 61% |
| D Comparative | cyclohexyl-CH< | 7 | 4-MeO-C$_6$H$_4$-CH< | — | 8 | Traces of product |
| E | 4-MeO-C$_6$H$_4$-CH< 1.1 eq | 4 | 4-MeO-C$_6$H$_4$-CH< 1.1 eq | 1.3 | 12 | Reaction complete 81% |
| F Comparative | 4-MeO-C$_6$H$_4$-CH< 1.1 eq | 4 | 4-MeO-C$_6$H$_4$-CH< | — | 13 | Traces of product |
| G | 4-MeO-C$_6$H$_4$-CH< 2.3 eq | 4 | — | 1.3 | 15 | Reaction complete 83% |
| H | 4-iPr-C$_6$H$_4$-CH< | 4 | 4-MeO-C$_6$H$_4$-CH< | 1.3 | 8 | Reaction complete 73% |
| I Comparative | 4-iPr-C$_6$H$_4$-CH< | 4 | 4-MeO-C$_6$H$_4$-CH< | — | 8 | Traces of product |
| J Comparative | —(CH$_2$)$_3$CH$_3$ | 2 | cyclohexyl-CH< | 1.3 | 20 | No reaction |

TABLE I-continued

| Exp. | R¹ | Time (h) | R | TMS-Cl (eq) | Time (h) | Results/ HPLC/yield |
|---|---|---|---|---|---|---|
| K Comparative | —(CH₂)₃CH₃ | 2 | 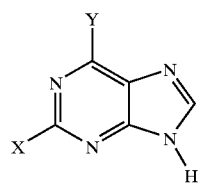 | — | 20 | No reaction |
| L | —(CH₂)₃CH₃ | 2 |  OMe | 0.5 | 9 | Reaction complete 74% |

The results in Table I clearly show that if a nonaromatic amine such as cyclohexyl amine is used as a reactant in the acid catalyzed process for preparing 2,6-diaminopurine derivatives, no reaction takes place. The results in Table I also show that aromatic amines, cycloaliphatic amines, and aliphatic amines may be used in the base catalyzed process for preparing 6-substituted aminopurine derivatives. In addition, the results in Table I show that an acid catalyst is necessary for the reaction in order to achieve a significant yield. It is further noted that in Experiment G, 2.3 equivalents of p-anisidine was added in the first step which was an excess wherein p-anisidine was available in the second step of the reaction to form the product.

While the invention has been described with particular reference to certain embodiments thereof, it will be understood that changes and modifications may be made by those of ordinary skill within the scope and spirit of the following claims.

What is claimed is:

1. A process for preparing 2,6-diaminopurine derivatives or an acid addition salt thereof comprising (i) reacting a purine compound having formula (V)

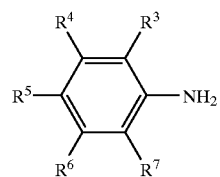

(V)

with an amine compound having formula (VI)

$$R^2—NH—R^1$$

(VI)

in the presence of a tertiary amine at a pH of 7 to 14 to form a 6-substituted aminopurine derivative having formula (I)

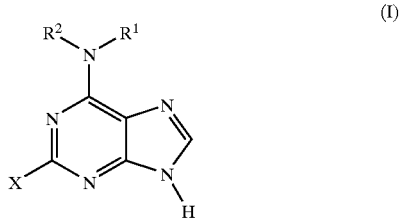

(I)

wherein X and Y are independently a halogen; and (ii) reacting the 6-substituted aminopurine derivative with an aromatic amine having formula (II)

(II)

in the presence of an acid catalyst at a pH of 0.1 to less than 7 to form 2,6-diaminopurine derivative having formula (III) or acid addition salt thereof

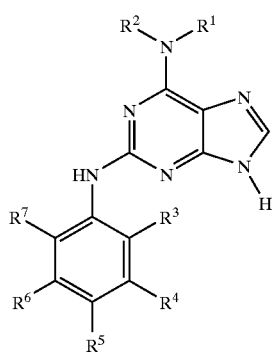

(III)

wherein X is a halogen; R¹ and R² are independently selected from the group consisting of hydrogen, alkyl, alkenyl, cycloalkyl, benzocycloalkyl, cycloalkylalkyl, aralkyl, heterocyclic group, alkoxy, and a group having formula (IV)

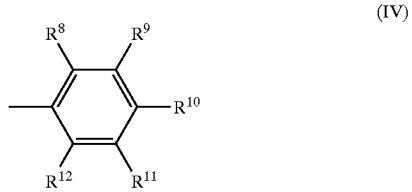

(IV)

$R^3$, $R^4$, $R^5$, $R^6$, $R^7$ $R^8$, $R^9$, $R^{10}$, $R^{11}$ and $R^{12}$ are independently selected from the group consisting of hydrogen, halogen, alkyl, alkoxy, —N($R^{13}$)$R^{14}$, —SO$_2$N($R^{15}$)$R^{16}$, $C_1$–$C_4$-alkylene-SO$_2$N($R^{15}$)$R^{16}$ and —CON($R^{17}$)$R^{18}$; or, when $R^1$ and $R^2$, or two of $R^3$, $R^4$, $R^5$, $R^6$, $R^7$$R^8$, $R^9$, $R^{10}$, $R^{11}$ and $R^{12}$, are attached to adjacent carbon atoms on the indicated benzene rings, they denote, together with the carbon atoms to which they are attached, a carbocyclic group having 5- to 10-ring atoms or a heterocyclic group having 5- to 10-ring atoms of which one, two or three are hetero atoms selected from the group consisting of nitrogen, oxygen and sulfur; $R^{13}$ is alkyl; $R^{14}$ is alkyl or —COR$^{19}$ wherein $R^{19}$ is selected from the group consisting of alkyl, haloalkyl, alkoxy, alkoxyalkyl, alkoxycarbonyl, and alkoxycarbonylalkyl; or $R^{13}$ and $R^{14}$, together with the nitrogen atom to which they are attached, denote a heterocyclic group having 5- or 6-ring atoms of which one or two are hetero atoms selected from nitrogen, oxygen and sulfur; $R^{15}$ is hydrogen or alkyl; $R^{16}$ is selected from the group consisting of hydrogen, alkyl, hydroxyalkyl, alkoxyalkyl, and alkoxycarbonylalkyl; or $R^{15}$ and $R^{16}$ together with the nitrogen atom to which they are attached denote a heterocyclic group having 5- or 6-ring atoms of which one or two are hetero atoms selected from nitrogen, oxygen and sulfur; and $R^{17}$ and $R^{18}$ are independently hydrogen or alkyl.

2. The process according to claim 1 wherein the 6-substituted aminopurine derivative is

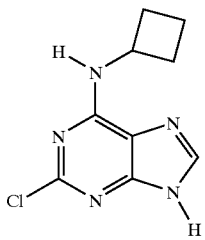

3. The process according to claim 1 wherein the 2,6-diaminopurine derivative is

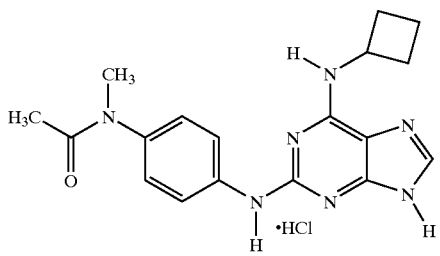

4. The process according to claim 1 which is a one-pot synthesis.

5. The process according to claim 1 wherein the pH in Step (i) is from about 7.5 to about 11.

6. The process according to claim 1 wherein the pH in Step (ii) is from about 0.5 to about 4.

7. The process according to claim 6 wherein the pH is from about 2 to about 3.

8. The process according to claim 1 wherein the temperature in Step (i) is from about 20° C. to about 150° C.

9. The process according to claim 8 wherein the temperature in Step (i) is from about 50° C. to about 130° C.

10. The process according to claim 9 wherein the temperature in Step (i) is from about 100° C. to about 120° C.

11. The process according to claim 1 wherein the temperature in Step (ii) is from about 20° C. to about 180° C.

12. The process according to claim 11 wherein the temperature in Step (ii) is from about 50° C. to about 140° C.

13. The process according to claim 12 wherein the temperature in Step (ii) is from about 70° C. to about 90° C.

14. The process according to claim 1 wherein the amine compound having formula (VI) is selected from the group consisting of cumidine, anisidine, chloroaniline, bromoaniline, fluoroaniline, cyclobutylamine, cyclohexylamine, cyclopentylamine, and N-(4-aminophenyl)-N-methyl-acetamide.

15. The process according to claim 14 wherein the amine compound is cyclobutylamine.

16. The process according to claim 1 wherein the aromatic amine having formula (II) is selected from the group consisting of cumidine, anisidine, chloroaniline, bromoaniline, fluoroaniline, and N-(4-aminophenyl)-N-methyl-acetamide.

17. The process according to claim 16 wherein the aromatic amine is N-(4-aminophenyl)-N-methyl-acetamide.

18. The process according to claim 1 wherein the acid catalyst is selected from the group consisting of triarylsilyl halide, trialkylsilyl halide, and alkylarylsilyl halide.

19. The process according to claim 1 wherein the acid catalyst is selected from the group consisting of trimethylsilyl chloride and thionyl chloride.

20. The process according to claim 1 wherein the acid catalyst is selected from the group consisting of a mineral acid, an organic carboxylic acid, and an organic sulfonic acid.

21. The process according to claim 17 wherein the acid catalyst is selected from the group consisting of hydrochloric acid, hydrobromic acid, benzoic acid, acetic acid, citric acid, propionic acid, phosphoric acid, fumaric acid, succinic acid, methanesulfonic acid, maleic acid, and sulfuric acid.

22. The process according to claim 21 wherein the acid catalyst is hydrochloric acid.

23. The process according to claim 1 which further comprises a solvent in Step (i).

24. The process according to claim 23 wherein the solvent is selected from the group consisting of $C_3$–$C_{12}$ alcohols, dimethylformamide, dioxan, tetrahydrofuran, N-methylpyrrolidinone, 2-methoxyethyl ether, ionic liquids, and combinations thereof.

25. The process according to claim 24 wherein the solvent is n-pentanol or n-butanol.

26. The process according to claim 1 wherein a solvent is used in Step (ii).

27. The process according to claim 26 wherein the solvent is selected from the group consisting of $C_3$–$C_{12}$ alcohols, dimethylformamide, dioxan, tetrahydrofuran, N-methylpyrrolidinone, 2-methoxyethyl ether, ionic liquids, and combinations thereof.

28. The process according to claim 27 wherein the solvent is n-pentanol or n-butanol.

29. The process according to claim 1 wherein the tertiary amine is selected from the group consisting of N,N-diisopropylethylamine, triethylamine, tripropyl amine, tributyl amine, ethyldimethylamine, and combinations thereof.

30. The process according to claim 29 wherein the tertiary amine is N,N-diisopropylethylamine.

* * * * *